United States Patent [19]

James et al.

[11] Patent Number: 5,286,902

[45] Date of Patent: Feb. 15, 1994

[54] PROCESS FOR PREPARATION OF 2-(6-METHOXY-2-NAPHTHYL)PROPIONIC ACID AND INTERMEDIATES THEREFOR UTILIZING 2,6-DIISOPROPYLNAPHTHALENE

[75] Inventors: Dustin K. James; Andrew P. Komin; John R. Siegman, all of Wichita, Kans.

[73] Assignee: Koch Industries, Inc., Wichita, Kans.

[21] Appl. No.: 685,529

[22] Filed: Apr. 15, 1991

[51] Int. Cl.$^5$ .............................................. C07C 51/16
[52] U.S. Cl. .................................... 562/418; 549/513; 568/430; 568/437; 568/575; 568/632; 568/736
[58] Field of Search ............................... 562/466, 418

[56] References Cited

U.S. PATENT DOCUMENTS

| | | |
|---|---|---|
| 2,751,418 | 6/1956 | Enos, Jr. . |
| 3,329,733 | 7/1967 | O'Grady . |
| 3,406,219 | 10/1968 | Oban . |
| 3,562,336 | 2/1971 | Nelson ............................ 562/466 |
| 3,637,767 | 1/1972 | Alvarez ............................ 562/466 |
| 3,651,148 | 3/1972 | Nelson . |
| 3,875,252 | 4/1975 | Haag et al. . |
| 3,958,012 | 5/1976 | Fried et al. . |
| 3,994,968 | 11/1976 | Alvarez . |
| 4,414,405 | 11/1983 | Giordano et al. . |
| 4,503,262 | 3/1985 | Gupton et al. . |
| 4,620,013 | 10/1986 | Uggeri et al. . |
| 4,906,790 | 3/1990 | Ishiguro et al. . |
| 4,929,771 | 5/1990 | Clausen et al. . |
| 4,994,607 | 2/1991 | Chan . |
| 5,003,113 | 3/1991 | Tanaka et al. . |

FOREIGN PATENT DOCUMENTS

| | | |
|---|---|---|
| 205215 | 12/1986 | European Pat. Off. . |
| 386848 | 9/1990 | European Pat. Off. . |

OTHER PUBLICATIONS

Wagner, "Synthetic Organic Chemistry," pp. 226–229, 235–237 & 249–252 (1953).

Aldrichimica Acta, vol. 12, No. 4, (1979), "Metal-Catalyzed, Highly Selective Oxygenations of Olefins and Acetylenes with tert-Butyl Hydroperoxide Practical Considerations and Mechanisms" (K. Barry Sharpless and Thomas R. Verhoeven, Dept. of Chemistry, Stanford University, Stanford, California), pp. 63–74.

Journal of Organic Chemistry, vol. 52, No. 2, (1987), "Selective Metal-Catalyzed Autoxidation of 2-Arylpropionaldehydes. An Improved Synthesis of Ibuprofen" (D. P. Riley, D. P. Getman, G. R. Beck, and R. M. Heintz, Monsanto Chemical Co., St. Louis, Missouri), pp. 287–290.

Tetrahedron Letters, vol. 30, No. 16, (1989), "Documenting the Scope of the Catalytic Asymmetric Dihydroxylation" (B. Bhushan Lohray, Thomas H. Kalantar, B. Moon Kim, Christine Y. Park, Tomoyuki Shibata, John S. Wai, and K. Barry Sharpless, Dept. of Chemistry, Massachusetts Institute of Technology, Cambridge, Massachusetts), pp. 2041–2044.

Journal of the American Chemical Society, vol. 112, No. 7, (1990) "Enantioselective Epoxidation of Unfunctionalized Olefins Catalyzed by (Salen)manganese Complexes" (Wei Zhang, Jennifer L. Loebach, Scott R. Wilson and Eric N. Jacobsen, Roger Adams Laboratory, Dept. of Chemistry, University of Illinois, Urbana, Illinois), pp. 2801–2803.

Report from Chem Systems, Report No. 87-8, "Manufacture of Some Nonstreoidal Anti-inflammatory Agents" (Process Evaluation/Research Planning), pp. 134–156, 159, 163–174 & 177–185 (1983–1984).

Primary Examiner—Michael L. Shippen
Attorney, Agent, or Firm—Shook, Hardy, & Bacon

[57] ABSTRACT

A process is disclosed for the synthesis of 2-(6-methoxy-2-naphthyl)propionic acid that utilizes 2,6-diisopropylnaphthalene.

36 Claims, No Drawings

PROCESS FOR PREPARATION OF 2-(6-METHOXY-2-NAPHTHYL)PROPIONIC ACID AND INTERMEDIATES THEREFOR UTILIZING 2,6-DIISOPROPYLNAPHTHALENE

This invention relates to the pharmaceutical industry, and more particularly, to a novel process for preparing 2-(6-methoxy-2-naphthyl)propionic acid and useful intermediates therefor.

BACKGROUND OF THE INVENTION

Naproxen is a common name for D-2-(6-methoxy-2-naphthyl)propionic acid which is known to be a nonsteroidal agent having anti-inflammatory, analgesic and antipyretic activity. South African Patent No. 67/07597 issued to Syntex as assignee in 1968 disclosed that 2-(napth-2'-yl) acetic and propionic acid derivatives were useful for therapeutic purposes. Since that time, the D-enantiomer of 2-(6-methoxy-2-naphthyl)propionic acid has proven particularly useful as a therapeutic agent and several synthesis processes have been developed in the art.

The propionic acid derivative, 2-(6-methoxy-2-naphthyl)propionic acid, exists as two enantiomers (D- and L-), also known as optical isomers, and the D-enantiomer sold as "naproxen" is known to be much more therapeutically potent than its L- ccunterpart. Therefore, during some phase of synthesis the D- and L-enantiomers are separated to provide the naproxen product. The prior art suggests two general schemes for preparing D-2-(6-methoxy-2-naphthyl)propionic acid. The first scheme encompasses several 2-stage methods wherein the first stage is organic synthesis of a racemic, (DL-) 2-(6-methoxy-2-naphthyl)propionic acid and the second stage comprises isolating the therapeutically effective D-enantiomer. Several methods for resolution of the optical isomers of 2-(6-methoxy-2-naphthyl)propionic acid are known in the art. For example, U.S. Pat. No. 3,637,767 issued to Syntex as assignee discloses reacting the racemic product with an optically active base to form a D-enantiomer salt. The salt is crystallized, separated and then recovered as D-2-(6-methoxy-2-naphthyl)propionic acid by acidification. U.S. Pat. No. 4,800,162 to Matson utilizes multi-phase and extractive enzyme membrane bioreactors as a means to produce substantiall purified optically active compounds from mixtures of active and inactive isomers.

A second general scheme for preparing naproxen focuses on asymmetric organic synthesis of the D-2-(6-methoxy-2-naphthyl)propionic acid product. These methods utilize optically pure starting materials or reagents, or may comprise stereo-selective synthesis steps. For example, European Patent No. 0,163,338 to Blaschim teaches using optically pure chiral reagents for direct stereo-specific synthesis.

The present invention is directed to providing an alternative process for the organic synthesis of racemic (DL-) 2-(6-methoxy-2-naphthyl)propionic acid, and also to providing intermediates for use in stereo-selective processes. It is known to synthesize racemic 2-(6-methoxy-2-naphthyl)propionic acid by various routes using 2-methoxynaphthalene as a starting material. A substituent is introduced at the C-6 position on the naphthalene nucleus via Freidel-Crafts acylation to yield a ketone intermediate 2-acetyl-6-methoxynaphthalene. [See U.S. Pat. No. 3,994,968 to Syntex as assignee]. The acylation may require halogenation or other methods to block substitution at other positions on the compound.

Several routes to the propionic acid derivative are known which utilize the ketone intermediate 2-acetyl-6-methoxynaphthalene heretofore described. For example, an early method known as the "Willgerodt/Methyl Iodide" process first prepares an acetic acid derivative from the ketone intermediate in the presence of morpholine and sulfur and then completes a series of steps including esterifying, methylating, and hydrolyzing the compound to produce (DL-)2-(6-methoxy-2-naphthyl)-propionic acid. [E.g. U.S. Pat. No. 3,994,968 issued to Syntex as assignee; U.S. Pat. No. 3,958,012 to Fried et al.]. Although this method has utility, the percent conversion from the ketone intermediate to the acid derivative product is relatively low (20% to 30%), whereas the cost of raw materials and reagents is relatively high.

Another method known in the art converts the ketone group of 2-acetyl-6-methoxynaphthalene to a 2-substituted propylene oxide using a trimethylsulfonium iodide reagent, followed by conversion to a propylene aldehyde and oxidation to the 2-substituted propionic acid. [U.S. Pat. Nos. 3,994,968 and 3,637,767 to Syntex as assignee]. The yields are higher (approximately 30% to 40%) than that observed with the Willgerodt-/Methyl Iodide process, however the yields are still too low to justify the high cost of the trimethylsulfonium iodide reagent and raw materials.

Other known routes include hydrocyanation of the carbonyl group of the ketone intermediate 2-acetyl-6-methoxynaphthalene followed by conversion to a 2-substituted propionic acid through a series of steps. This method has about a 30% to 40% conversion as well and calls for expensive reagents such as triethylaluminum. Other process steps for the preparation of 2-(6-methoxy-2-naphthyl)propionic acid are known which utilize intermediates derived from the acylated 2-methoxynaphthalene as starting or intermediate materials. [E.g. U.S. Pat. No. 4,414,405 to Giorano; U.S. Pat. No. 4,620,031 to Uggeri; U.S. Pat. No. 3,651,148 to Nelson et al.].

Although the above conventional routes have utility, using 2-methoxynaphthalene as a starting material (or its precursor 2-naphthol) is expensive, partially due to industry demand, to the high cost of reagents, and to disposal of waste products. There is need for a process that utilizes inexpensive materials and results in a high yield of product.

It is therefore a primary object of this invention to provide a process for the organic synthesis of 2-(6-methoxy -2 -naphthyl)propionic acid that utilizes readily available and inexpensive starting material of fixed isomeric purity.

It is a further object of this invention to provide a process for the organic synthesis of 2-(6-methoxy-2-naphthyl)propionic acid that utilizes 2,6-diisopropyl-naphthalene as a starter material.

Another object of this invention is to provide a process for the organic synthesis of 2-(6-methoxy-2-naphthyl)propionic acid that does not require Friedel-Crafts acylation.

It is still a further object of this invention to provide a process for the organic synthesis of 2-(6-methoxy-2-naphthyl)propionic acid having a high percent of conversion of 2,6-diisopropylnaphthalene to 2-(6-methoxy-2-naphthyl)propionic acid.

A further object of this invention is to provide a process for the organic synthesis of 2-(6-methoxy-2- naphthyl)propionic acid whereby the unreacted products and reaction reagents are recyclable.

It is another object of the present invention to provide a process for the organic synthesis of 2-(6-methoxy-2-naphthy)propionic acid that eliminates waste associated with the use of some conventional method reagents.

It is still another object of the present invention to provide a process for the organic synthesis of 2-(6-methoxy-2-naphthyl)propionic acid whereby the reagents are inexpensive and some of the needed reactants are provided by the process.

Another object of the present invention is to provide ga process for the organic synthesis of 2-(6-methoxy-2-naphthyl)propionic acid wherein several steps can be run continuously, thereby lowering capital costs and increasing throughout.

It is also a object of the present invention to provide a process for the organic synthesis of 2-(6-methoxy-2-naphthyl)propionic acid that can be used in combination with other processes to asymmetrically prepare D-2-(6-methoxy-2-naphthyl)propionic acid.

A further object of the present invention is to provide a process for the organic synthesis of 2-(6-methoxy-2-naphthyl)propionic acid which produces intermediates applicable to other synthesis processes.

These and other objects are achieved by a novel process for preparing 2-(6-methoxy-2-naphthyl)propionic acid and the intermediates therefor, a preferred route exemplified as follows:

propylnaphthalene; Formula V is 2-methoxy-6-(1-hydroperoxy-1-methylethyl)naphthalene; Formula VI is 2-methoxy-6-isopropenylnaphthalene; Formula VII 2-(6-methoxy-2-naphthyl)-1-propylene oxide; Formula VIII is 2-methoxy-6-(1-hydroxy-1-methylethyl)naphthalene; Formula IX is 2-(6-methoxy-2-naphthyl)propionaldehyde; and Formula X is 2-(6-methoxy-2-naphthyl)propionic acid.

STEP A

The starting material for the process of the present invention is 2,6-diisopropylnaphthalene (DIPN) which is a readily available material useful in preparing polymer intermediates. In Step A of the present process, the DIPN of Formula I is converted to the 2-(1-hydroperoxy-1-methylethyl)-6-(1-methylethyl)naphthalene of Formula II via hydroperoxidation. The hydroperoxidation of Step A can be effected in the presence of oxygen and a catalyst at or near reflux temperatures.

Several catalyst systems are known and can be used for the hydroperoxidation Step A. For example, a catalytically active heavy metal compound, such as cobalt, copper, lead, iron, mercury, vanadium, and chromium metal compounds or finely divided noble metal such as palladium or platinum can be used as the catalyst.

The preferred catalyst system for Step A is an alkali earth metal salt of an organic or inorganic acid such as carboxylic acid, sulfonic acid, or phosphoric acid, with carboxylic acid being preferred. The following are ex-

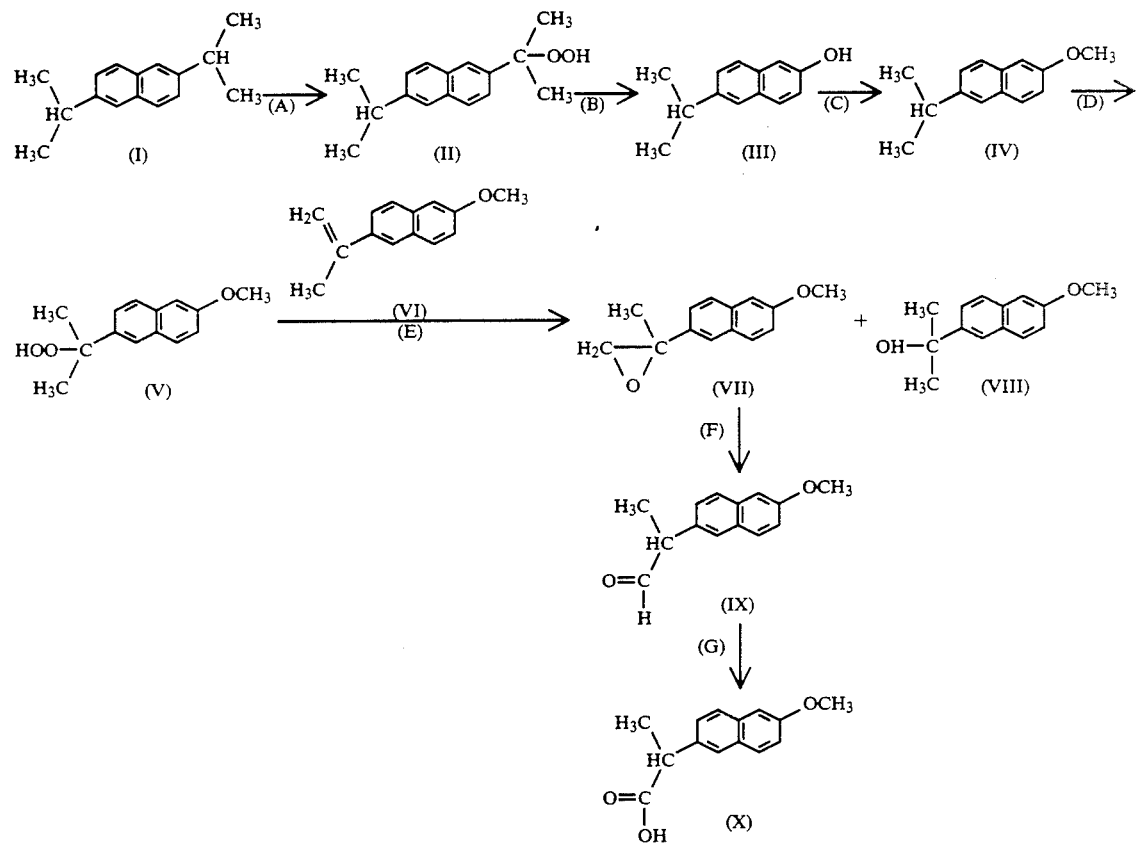

Formula I is 2,6-diisopropylnaphthalene; Formula II is 2-(1-hydroperoxy-1-methylethyl)-6-(1-methylethyl)naphthalene; Formula III is 2-hydroxy-6-(1-methylethyl)naphthalene; Formula IV is 2-methoxy-6-isoamples of suitable organic carboxylic acids whose salts can be utilized as the catalyst: n-valeric acid, caproic acid, n-heptanoic acid, caprylic acid, pelargonic acid, capric acid, lauric acid, myristic acid, 2-ethyl-butyric acid, 4-ethylhexanoic acid or 3-ethylheptanoic acid and preferable, 2-ethylcaproic acid. The salts of these acids can be formed in situ, for example the organic carboxylic acids and either an alkali metal hydroxide or alkaline earth metal hydroxide can be added to the reaction mixture separately to form the salt catalyst for the hydroperoxidation. The alkali earth metal salt not only acts as a catalyst, but also as a soap or emulsifier to prevent the system from becoming too acidic. This is desirable because highly acidic conditions tend to decompose the hydroperoxide derivative and result in the production of secondary byproducts. The acid salts are preferably used in amounts of 0.01 to 2.0%, and more preferably 0.02 to 1.0%, and most preferably 0.05 to 0.1% by weight relative to the weight of the DIPN starting material.

In carrying out the hydroperoxidation of Step A, it is preferable to employ reaction initiators to induce conversion. Organic free radical formers such as peroxides, e.g. tert-butyl hydroperoxide, cumene hydroperoxide, and diisopropylnaphthalene-mono-hydroperoxide; and azo compounds, e.g. azobisisobutyronitrile are particularly useful. Alternatively, light can be used to generate the free radicals. Most preferably, the initiator is a mono-hydroperoxide derivative such as 2-(1-hydroperoxy-1-methylethyl)-6-(1-methylethyl)naphthalene and 2-methoxy-6-(1-hydroperoxy-1-methylethyl)naphthalene produced by Step A and Step D of the present invention respectively, thereby eliminating the need to purchase additional reagents. About 0.05 to 3.0%, preferably 0.1 to 2.0% by weight and most preferably 0.5 to 1.0% by weight initiator, relative to the weight of DIPN (Formula I) is added to the reaction mixture.

A solvent may optionally be used in Step A for maintaining a lower temperature of reaction. Suitable solvents include aliphatic hydrocarbons, e.g. hexane, heptane, pentane, and octane; aromatic hydrocarbons, e.g. benzene, toluene, xylenes, pseudocumene, and mesitylene; or any other solvent compatible with DIPN such as fluorene, biphenyl, and naphthalene. Preferably, the solvent is an aliphatic hydrocarbon and most preferably the solvent is heptane. A solvent is not required however, and neat DIPN can be used for the reaction of Step A.

A basic aqueous phase can also optionally be added to the DIPN reaction mixture of Step A. The basic phase may be formed using as the base any alkali metal compound, such as hydroxides, carbonates, phosphates and acetates, e.g. sodium hydroxide, potassium hydroxide, sodium carbonate, potassium carbonate, potassium phosphate, sodium acetate or potassium acetate. The basic phase is helpful in reducing acidity levels in the mixture as the reaction proceeds. High acidity tends to decrease the oxidation rate and results in low hydroperoxide yields.

The reaction mixture of Step A is heated to the range of about 20° to 160° C., and preferably to about 80° to 120° C. This is an exothermic reaction and continuous heating may not be required. Cooling coils may preferably be used to control the reaction temperature. The oxygen source for Step A is released into the system, and can be molecular oxygen or gases containing oxygen such as air. Optionally, oxygen donors, such as ozone can be used as the actual oxidizing agent in the process. The gas pressure utilized can range from atmospheric pressure to about 7,000 kilopascals (kPa). Sparging the reaction system with gas under pressure is instrumental in bringing the oxygen into intimate contact with the liquid phase. About 0.1 to 1 meters cubed ($m^3$) and preferably about 0.3 to 0.6 $m^3$ of oxygen gas per kilogram of DIPN is passed through the reaction mixture per hour.

The reaction time for Step A ranges from approximately 1 to 36 hours, and is preferably about 6 to 12 hours. The hydroperoxide derivative of Formula II is relatively unstable in the presence of acids and tends to decompose with high yields of product. It is therefore advantageous to keep the percent conversion of DIPN to the 2-(1-hydroperoxy-1-methylethyl)-6-(1-methylethyl)naphthalene product relatively low, preferably to stop the reaction at a conversion of 10 to 35%, and most preferably at 15 to 20%. The conversion can be monitored by known methods such as gas chromatography, high performance liquid chromatography, thin layer chromatography or iodometric titration, to determine the amount of 2-(1-hydroperoxy-1-methylethyl)-6-(1-methylethyl)naphthalene in the reaction mixture. When the desired yield has been reached, the mixture is cooled to prevent further reaction. The unreacted DIPN of Formula I is recovered in Step B and can be recycled for use in Step A.

STEP B

In Step B the 2-(1-hydroperoxy-1-methylethyl)-6-(1-methylethyl)naphthalene of Formula II is heated to reflux temperatures in the presence of an acid catalyst to form the 2-hydroxy-6-(1-methylethyl)naphthalene of Formula III and an acetone by-product. A compatible solvent can be added directly to the reaction mixture of Step A containing the hydroperoxide derivative product (Formula II) and the unreacted DIPN of Formula 1. Suitable solvents include alcohols e.g. methanol, ethanol, isopropanol, and propanol; ketones e.g. acetone, methylethylketone, and cyclo-hexanone; and aliphatic or aromatic hydrocarbons e.g. heptane, toluene, octane, xylene, and hexane. Preferably the solvent is a lower alcohol, and more preferably is methanol.

An acid catalyst is added to the 2-(1-hydroperoxy-1-methylethyl)-6-(1-methylethyl)naphthalene reaction mixture in catalytic amounts while heating the mixture to reflux temperatures. A mineral acid such as hydrochloric acid, sulfuric acid, phosphoric acid, or perchloric acid is useful for this purpose; preferably concentrated hydrochloric or sulfuric acid and most preferably concentrated hydrochloric acid. The reaction continues until the hydroperoxide derivative produced in Step A (Formula II) is consumed; that is until it is no longer detectable in the mixture. The temperature of reaction is in the range of 20° to 140° C., preferably 50° to 100° C., and most preferably about 75° C. or reflux temperature. If needed, the acetone can be removed by distillation as it is formed.

After the hydroperoxide derivative of Formula II is completely consumed in Step B, the solvent and acetone byproduct (if not already removed) are removed by conventional means. The resulting solution is extracted with an aqueous alkali metal hydroxide solution, and in particular with a solution of sodium hydroxide or potassium hydroxide. The unreacted 2,6-diisopropylnaphthalene (DIPN) from Step A and other neutral compounds remain in the organic phase, and the 2-hydroxy-6-(1-methylethyl)naphthalene of Formula III is now in the alkaline aqueous phase. The organic layer can be concentrated to recover and recycle the DIPN of Formula I for use in Step A.

The alkaline aqueous phase resulting from the extraction of Step B contains the 2-hydroxy-6-(1-methylethyl)naphthalene of Formula III. This aqueous phase can be acidified with mineral acid, preferably a strong mineral acid such as sulfuric acid or hydrochloric acid to precipitate the hydroxy derivative product. Optionally, the alkaline aqueous layer containing the hydroxy derivative of Formula III can instead be used directly in Step C.

STEP C

In Step C the 2-hydroxy-6-(1-methylethyl)naphthalene of Formula III is alkylated to form the 2-methoxy-6-isopropylnaphthalene of Formula IV. The alkylation can be accomplished by heating the 2-hydroxy-6-(1-methylethyl)naphthalene in the presence of a solvent, a base, and a methyl donor to reflux temperatures. A compatible solvent such as water, tetrahydrofuran, hexamethylphosphortriamide, dimethyl sulfoxide, N,N-dimethylformamide or dioxane, and, most preferably water is added to the isolated hydroxy derivative of Formula III. At least one mole equivalent of a base, relative to the amount of 2-hydroxy-6-(1-methylethyl)-naphthalene is also added to the aqueous mixture containinq Formula III. Suitable bases include sodium hydroxide, potassium hydroxide, potassium carbonate and sodium carbonate, preferably sodium hydroxide.

Optionally, the alkaline solution in Step B can be used directly as the reaction mixture for Step C. Rather than isolating the product of Step B (Formula III) by precipitating the product, the alkaline solution is used directly in Step C, thereby eliminating the need for addition of the solvent and base heretofore described.

Any methyl donor capable of alkylating an anion can be used in Step C. Examples of suitable methyl donors include dimethyl sulfate, methyl iodide, methyl chloride, methyl bromide, methyl sulfonate, methyl tosylate, methyl triflate and methyl bisulfate, wherein methyl chloride or dimethyl sulfate are preferred.

The temperature of reaction for Step C is the reflux temperature and may range from 20° to 120° C. The temperature of reaction is dependent to some degree upon the methyl donor; for example, when using dimethyl sulfate, the temperature can be about 60° C., whereas with methyl chloride the temperature should be above 80° C. The pressure can range from ambient air pressure to 700 kPa, and the reaction should be run at pressures above ambient for the higher temperature methyl chloride reaction.

The reaction of Step C is complete when the pH of the reaction mixture drops to 7 or below, or when the pressure begins to drop. Other conventional analytical techniques heretofore described for detecting the amount of a compound in the mixture can alternatively be used. When the reaction is complete, the mixture is cooled preferably to a temperature in the range of about 0° to 20° C., and most preferably to about 5° C. The cooling process precipitates the 2-methoxy-6-isopropyl-naphthalene product (Formula IV) of Step C. The solid product can be isolated by filtration or by extraction with toluene or other suitable solvents followed by washing, drying, filtering, concentrating and recrystallizing the solid from, for example, isopropanol.

An alternative method for preparing the 2-methoxy-6-isopropylnaphthalene of Formula IV is by catalytically alkylating 2-methoxynaphthalene in the presence of an isopropylating agent. Isopropylating agents in general are propyl groups with leaving groups e.g. 2-propanol, 2-propylhalide, 2-propylesters; or olefins, e.g. propylene. The catalyst is preferably a shape selective zeolite catalyst such as a mordenite that produces product enriched in the 2-methoxy-6-isopropylnaphthalene isomer when compared to non-shape selective catalysts. The mordenite may be modified by dealuminization, metal modification, surface coating modification and combinations thereof to enhance shape selectivity to 2-methoxy-6-isopropylnaphthalene. Most preferably, the catalyst is a dealuminized mordenite.

The 2-methoxynaphthalene, either neat or in an appropriate solvent, is treated with the isopropylating agent in the presence of the catalyst at atmospheric to superatmospheric pressure, e.g. 0 to 3500 kPa, preferably 0 to 1000 kPa, and at a temperature in the range of 200° to 325° C., preferably 200° to 250° C. The catalyst is separated by filtration and the 2-methoxy-6-isopropylnaphthalene of Formula IV and an unreacted 2-methoxynaphthalene is recovered by distillation from the solvent, if a solvent is used. The product of this shape selective process can then be used as the 2-methoxy-6-isopropylnaphthalene of Formula IV in the following steps.

STEP D

In Step D the 2-methoxy-6-isopropylnaphthalene of Formula IV is hydroperoxidized to form the 2-methoxy-6-(1-hydroperoxy-1-methylethyl)naphthalene of Formula V. This conversion can be accomplished by several known hydroperoxidation methods. As described in Step A, the preferred method comprises heating the 2-methoxy-6-isopropylnaphthalene of Formula IV to or near reflux temperatures in the presence of an oxygen source, an alkali metal salt of an organic or inorganic acid, and optionally a free radical initiator, a solvent and a basic aqueous phase. The reaction conditions and suitable reagents are fully disclosed in Step A.

A low percent of conversion from the 2-methoxy-6-isopropylnaphthalene product of Step C to the 2-methoxy-6-(1-hydroperoxy-1-methylethyl)naphthalene of Formula V is again preferred wherein the conversion preferably ranges from 10% to 35% and most preferably from 15% to 25%. The conversion is monitored by aforementioned known analytical techniques for determining the amount of compound in the mixture and the reaction mixture is cooled upon reaching the desired yield.

The 2-methoxy-6-(1-hydroperoxy-1-methylethyl)-naphthalene can be extracted into an aqueous phase with an inorganic base, and is preferably with dilute sodium hydroxide or potassium hydroxide. The aqueous phase is separated by conventional means and a second alkaline extraction is performed. The combined aqueous layers are back extracted with any compatible organic solvent such as toluene and the aqueous layer is neutralized with solid or gaseous carbon dioxide. The 2-methoxy-6-(1-hydroperoxy-1-methylethyl)naphthalene of Formula V crystallizes out of solution and is filtered and water washed.

Alternatively, the cooled reaction solution may be utilized without isolation of the 2-methoxy-6-(1-hydroperoxy-1-methylethyl)napthalene. The crude mixture of the hydroperoxide derivative of Formula V and the starting material of Formula IV can be used directly in the next reaction after filtering off insoluble materials and removing some of the solvent by distillation.

STEP E

In Step E, the 2-methoxy-6-(1-hydroperoxy-1-methylethyl)naphthalene product of Step D (Formula V) is reacted with the 2-methoxy-6-isopropenylnaphthalene of Formula VI in the presence of a solvent and a catalyst at reflux temperatures to form the epoxide derivative 2- 6-methoxy-2-naphthyl)propylene oxide of Formula VII and 2-methoxy-6-(1-hydroxy-1-methylethyl)naphthalene of Formula VIII.

The hydroperoxide derivative of Formula V and the olefin derivative of Formula VI are dissolved in a compatible solvent, preferably in ethylene dichloride, toluene or xylene, and, most preferably ethylene dichloride having a concentration of about 1 molar. An oxidation catalyst, preferably a molybdenum or vanadium catalyst such as molybdenum hexacarbonyl, molybdenum acetylacetonate, molybdenum trioxide, molybdenum blue or vanadyl acetylacetonate is added to the reaction mixture of Step E. The amount of catalyst added can range from 0.01 to 10.0 mole %, preferably about 0.05 to 0.5 mole %, and most preferably about 0.25 mole % based on either the amount present of 2-methoxy-6-(1-hydroperoxy-1-methylethyl)naphthalene (Formula V) or 2-methoxy-6-isopropenylnaphthalene (Formula VI).

An acid scavenger can optionally be added to the reaction mixture of Step E such a disodium hydrogen phosphate or a tertiary amine such as triethylamine, trimethylamine or 4-methyl-morpholine. The scavenger is added in an amount ranging from 0.1 to 10.0 mole % and preferably from 0.5 to 2.0 mole %, relative to the amount of either the 2-methoxy-6-(1-hydroperoxy-1-methylethyl)naphthalene (hydroperoxide derivative) or the 2-methoxy-6-isopropenylnaphthalene (olefin derivative).

The mixture is heated to or near reflux temperatures ranging from 20° to 120° C. and preferably 60° to 80° C. Conventional means heretofore mentioned can be utilized to determine when all of either the olefin or hydroperoxide derivative is consumed. The reaction mixture is cooled and quenched with, for example, an aqueous sodium sulfite solution to remove any residual peroxides. The organic solution is distilled to purify the products, or concentrated under vacuum and subjected to chromatography or crystallization to give the epoxide derivative, 2-(6-methoxy-2-naphthyl)-1-propylene oxide of Formula VII, and the alcohol derivative, 2-methoxy-6-(1-hydroxy- 1-methylethyl)naphthalene of Formula VIII.

An alternative second route for preparation of the epoxide intermediate, 2-(6-methoxy-2-naphthyl)-1-propylene oxide, is exemplified below:

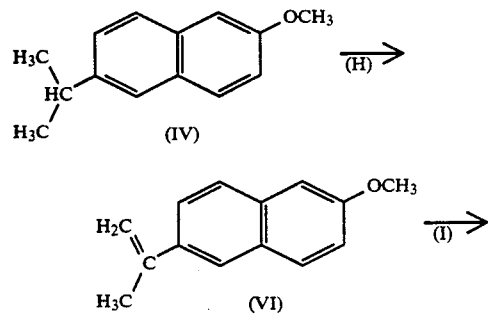

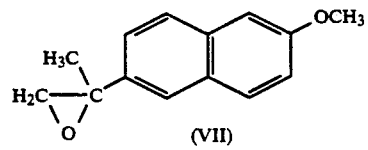

These process steps replace Steps D and E heretofore described. In Step H the 2-methoxy-6-isopropylnaphthalene of Formula IV can be dehydrogenated in the presence of a metal catalyst to form the olefin derivative 2-methoxy-6-isopropenylnaphthalene of Formula VI. Suitable catalysts include metal oxides e.g. iron oxide, nickel oxide, zinc oxide, and magnesium oxide; or other metal catalysts such as chromium on alumina, copper chromite, barium promoted copper chromite, barium/manganese promoted copper chromite, vanadia, vanadium on silica, nickel on refractory alumina, nickel and iron/potassium/chromium catalysts.

A solvent can also, optionally, be present in the reaction mixture of Step H such as an aromatic hydrocarbon, e.g. benzene, toluene, xylene, biphenyl, naphthalene, isodurene, pseudocumene, mesitylene; or aliphatic hydrocarbons e.g. heptane, octane, nonane, decane, and isomers thereof. The reaction temperature can range from 250° to 800° C. at a pressure of 10 to 1,013,000 kPa. A carrier gas is fed into the reactor at such a rate as to produce maximum conversion and selectivity. The carrier gas is preferably nitrogen, helium, argon, or carbon dioxide.

Preferably, the reaction of Step H is conducted in a tube furnace wherein the tube is packed with supported or unsupported catalyst. The 2-methoxy-6-isopropylnaphthalene of Formula IV, is provided neat or in solution, and fed into the reactor along with a carrier gas at a rate of maximum conversion and selectivity. The olefin derivative product, 2-methoxy-6-isopropenylnaphthalene of Formula VI, can be distilled or crystallized from the unreacted starting material.

The 2-methoxy-6-isopropenylnaphthalene product of Step H (Formula VI) is a required reactant for Step E of the preferred route heretofore described. Therefore the 2-methoxy-6-isopropenylnaphthalene of Formula VI required for Step E can be produced by dehydrogenating (Step H) a portion of the 2-methoxy-6-isopropylnaphthalene product of Step C.

In the alternative, the 2-methoxy-6-isopropenylnaphthalene of Formula VI can be epoxidized in Step I. In this step, the olefin derivative is reacted with any commercially available hydroperoxide such as hydrogen peroxide, cumene hydroperoxide or tert-butyl hydroperoxide to form the 2 (6-methoxy-2-naphthyl) propylene oxide of Formula VII and an alcohol. This Step is similar to the epoxidation reaction heretofore described in Step E, differing only as to the choice of hydroperoxide derivative reacted with the 2-methoxy- 6-isopropenylnaphthalene. The 2-methoxy-6-isopropenylnaphthalene is reacted with the hydroperoxide in the presence of a solvent and catalyst at or near reflux temperatures. The preferred reaction conditions and reagents as fully disclosed above for Step E.

A second alternative route for preparation of the epoxide intermediate, is represented schematically below:

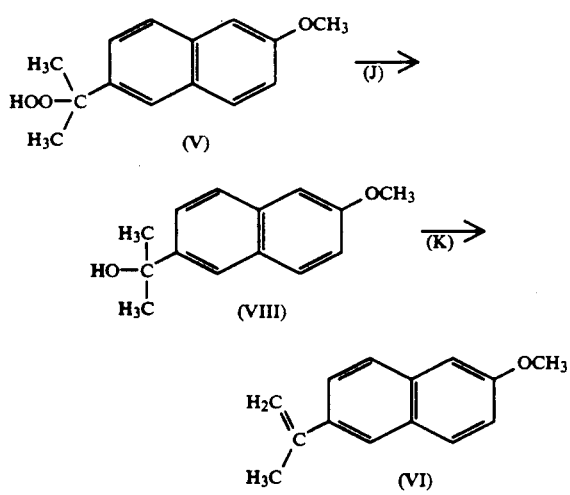

The above depicted steps replace Step E of the preferred route heretofore described. In Step J, the 2-methoxy-6-(1-hydroperoxy-1-methylethyl)naphthalene of Formula V is reacted with a olefin and in particular with any commercially available lower alkene such as ethene, propene or butene to form the 2-methoxy-6-(1-hydroxy-1-methylethyl)naphthalene of Formula VIII and an epoxide derivative respectively. This reaction is similar to Step E heretofore described, differing only with respect to choice of the olefin derivative reacted with 2-methoxy-6-(1-hydroperoxy-1-methylethyl)naphthalene. The reaction conditions and reagents for Step J are the same as herein disclosed for Step E.

In Step K, the 2-methoxy-6-(1-hydroxy-1-methylethyl)naphthalene of Formula VIII is dehydrated to form the 2-methoxy- 6-isopropenylnaphthalene of Formula VI. The dehydration is affected by heating the 2-methoxy-6-(1-hydroxy-1-methylethyl)naphthalene to a temperature ranging from 60° to 250° C. Optionally a catalyst can additionally be present to facilitate the dehydration. Suitable catalysts include toluenesulfonic acid, hydrochloric acid, sulfuric acid, clay and molecular sieves. The pyridine or other tertiary amine salt of inorganic acids can also be used as a catalyst to facilitate dehydration. Such salts are exemplified by pyridine hydrochloride, pyridine hydrobromide, triethylamine hydrochloride, triethylamine hydrobromide, pyridine sulfate, and triethylamine sulfate. A solvent such as tetrahydrofuran, hexamethylphosphortriamide, toluene, xylene, N,N-dimethylformamide or ethyl acetate may be utilized in Step K.

The 2-methoxy-6-isopropenylnaphthalene prepared in Step K can be utilized as the required reagent in the epoxidation of Step E heretofore described. The 2-methoxy-6-(1-hydroxy-1-methylethyl)naphthalene of Formula VIII can be provided for Step K by practicing Step E of the preferred route wherein 2-methoxy-6-(1-hydroxy-1-methylethyl)naphthalene is a by-product of the epoxidation Step E. The 2-methoxy-6-isopropenylnaphthalene of Formula VI can alternatively be epoxidized to form the 2-(6-methoxy-2-naphthyl) propylene oxide of Formula VII a disclosed in Step I heretofore described.

The most preferred method for practicing this invention is to (1) follow the preferred route disclosed as Steps A through G, (2) initially produce the 2-methoxy-6-isopropenylnaphthalene of Formula VI required in Step E by dehydrogenating (Step H) some of the 2-methoxy-6-isopropylnaphthalene of Formula IV, and (3) further supplying the reaction system of Step E with the 2-methoxy-6-isopropenylnaphthalene of Formula VI by converting the by-product alcohol of Step E, 2-methoxy-6-(1-hydroxy-1-methylethyl)naphthalene (Formula VIII) to the 2-methoxy-6-isopropenylnaphthalene of Formula VI a disclosed in Step K.

STEP F

In Step F the 2-(6-methoxy-2-naphthyl)-1-propylene oxide of Formula VII is converted to the 2-(6-methoxy-2-naphthyl)propionaldehyde of Formula IX by any conventional means. For example, the 2-(6-methoxy-2-naphthyl)-1-propylene oxide can be heated in the absence of a catalyst at a temperature sufficient to affect conversion to the aldehyde derivative, preferably heated to above 220° C. either with or without an inert organic solvent. Alternatively, the epoxide derivative of Formula VII is melted without solvent at a temperature above 120° C. and preferably from 120° to 160° C. in the presence of a Lewis acid. In a preferred method, the 2-(6-methoxy-2-naphthyl)-1-propylene oxide product of Step E (Formula VII) is dissolved in an inert organic solvent system and a Lewis acid is added to the mixture. The reaction temperature of this preferred method is much lower, ranging from 0° to 30° C., and preferably from 5° to 10° C. The preferred reaction is conducted in an inert atmosphere such as nitrogen, for example.

Examples of suitable Lewis acids include boron trifluoride etherate, boron trifluoride, boron trichloride, aluminum chloride, zinc chloride, and stannic chloride, the preferred Lewis acid being boron trifluoride etherate. Any compatible inert organic solvent can be utilized, and a particularly suitable inert organic solvent is tetrahydrofuran. The product 2-(6-methoxy napthyl)propionaldehyde of Formula IX can be separated from the reaction mixture by any conventional means, or the mixture can be concentrated to usable form for the next process Step G by distillation under reduced pressure. Preferably a base such as pyridine, for example, is added prior to the distillation.

As an alternative, the aldehyde derivative of Formula IX can be prepared by oxidizing the olefin derivative of Formula VI. The olefin derivative is prepared by dehydrogenating 2-methoxy-6-isopropylnaphthalene of Formula IV as previously described in Step H. The olefin derivative, 2-methoxy-6-isopropenylnaphthalene is oxidized in the presence of oxygen and a catalyst to form the aldehyde derivative of Formula IX. This transformation can be carried out in the presence of catalysts known in the art for similar transformations. Examples of suitable catalysts include palladium chloride, palladium diacetate, $(MeCN)_2PdCl_2$, $(C_6H_5CN)_2PdCl_2$, $(MeCN)_2PdClNO_2$, and $(C_6H_5CN)_2PdClNO_2$. The preferred catalyst is $(MeCN)_2PdClNO_2$. In order to minimize the use of expensive palladium catalysts, a co-catalyst such as copper chloride can be present. Suitable solvents include water, methanol, ethanol, propanol, isopropanol, butanol, 2-butanol, tert-butanol, acetic acid, toluene, benzene, dichloromethane, ethylene dichloride, chlorobenzene, acetonitrile, benzonitrile, and similar solvents or mixtures thereof. The preferred solvent is tert-butanol. The reaction can be carried out at temperatures ranging from 25° to 100° C., with 40° to 80° C. being preferred. Oxygen can be provided to the reaction by bubbling in air, oxygen, or mixtures of oxygen with nitrogen, argon, or other inert gases. Alternatively, the solvent can be presaturated with air or oxygen before adding the substrate. The reaction time can be from 2 to 24 hours, with 6 to 8 hours being preferred.

The product can be recovered from the reaction by concentration and distillation, crystallization, or chromatography of the residue. In some cases, when hydroxylic solvents such as methanol and ethanol are used, the aldehyde is partially or totally recovered as its corresponding dialkyl acetal. In this case, an aqueous acidic work-up leads to reformation of the aldehyde.

STEP G

In Step G, the 2-(6-methoxy-2-naphthyl)propionaldehyde of Formula IX is oxidized to form the 2-(6-methoxy-2-naphthyl)propionic acid of Formula X by any method known for the oxidation of aldehydes to acids. Air oxidation of aldehydes to acids is well known in the art. For examples see *J. Organic Chemistry* 1987 Vol. 52 (287–290). In a preferred method, the 2-(6-methoxy-2-naphthyl)propionaldehyde is oxidized in the presence of a chromic acid solution at reflux temperatures. This oxidation is carried out in a mixture of acetone and an aqueous solution of chromic acid having a normality of six to ten and preferably about eight. The reaction mixture is cooled, wherein the reaction temperature ranges from −20° to 10.0° C., and preferably from −5° to 0.0° C. The chromic acid solution can be prepared from water, chromium trioxide and sulfuric acid by known procedures. The product can be separated from the reaction mixture by diluting the mixture with water, separating the precipitated solid, and washing and drying to yield the 2-(6-methoxy-2-naphthyl)-propionic acid of Formula X.

In another preferred method, the aldehyde of Formula IX is converted to its oxime using hydroxlamine hydrochloride or hydroxylamine sulfate in any one of several methods known for conversion of aldehydes to oximes. The oxime, with or without isolation, is then heated with an excess of sodium hydroxide or potassium hydroxide in ethylene glycol, diethylene glycol, or other glycol solvent to temperatures appropriate for conversion of the oxime into the sodium or potassium salt of the acid derivative of Formula X, such as 160° to 250° C. The 2-(6-methoxy-2-naphthyl)propionic acid is then isolated by acidifying the cooled solution with hydrochloric acid, sulfuric acid, or other mineral acid to precipitate the acid derivative.

In another preferred method for the oxidation of the aldehyde derivative of Formula IX to the propionic acid derivative of Formula X, a sodium bisulfite adduct of the aldehyde derivative is utilized as an intermediate to yield the acid derivative. This method is known in the art (Wuts, P.G.M.; Bergh, C. L. *Tetrahedron Letters*, 1986 (27) 3995).

Alternative Routes for Preparation of 2-(6-methoxy-2-naphthyl)propionaldehyde IX and 2-(6-methoxy-2-naphthyl)propionic acid X As an alternative route for the preparation of the aldehyde derivative of Formula IX and the acid derivative of Formula X and to demonstrate that the process provides intermediates applicable to other synthesis processes, the intermediate 6-isopropenyl-2-methoxynaphthalene VI can be converted to the aldehyde derivative or the acid derivative by the following route:

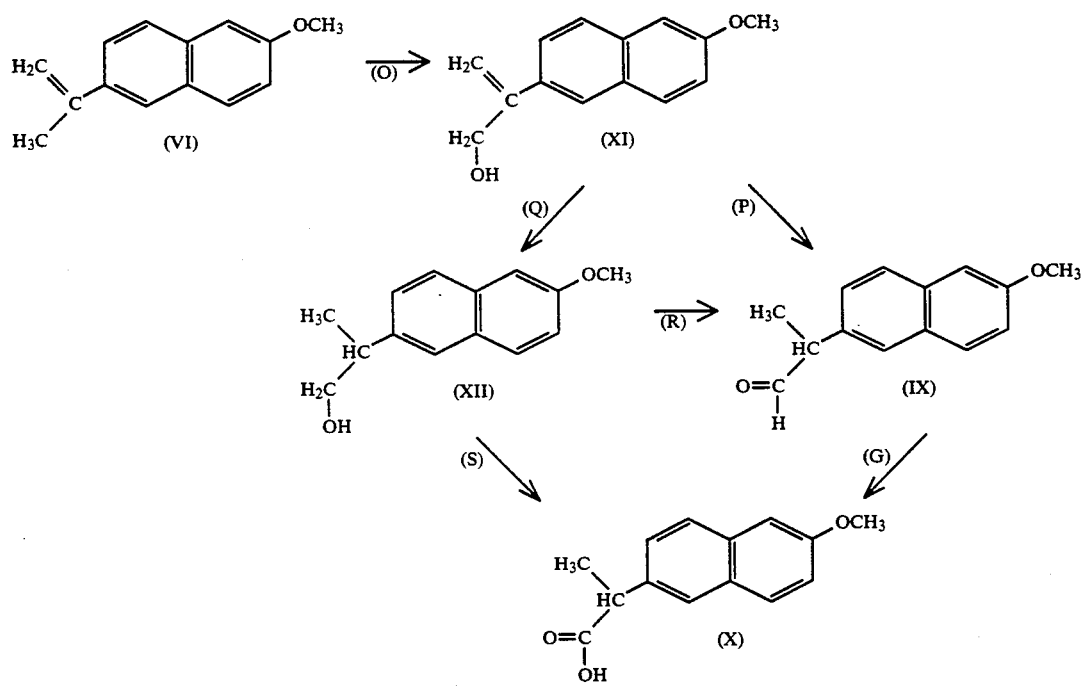

In Step O of this alternate end route, the olefin derivative of Formula VI is converted to a new intermediate compound, the allylic alcohol derivative 2-(6-methoxy-2-naphthyl)prop-2-en-1-ol of Formula XI. This new compound is a useful intermediate for the synthesis routes herein disclosed as well as other racemic or stereo-selective synthesis processes. This conversion occurs in the presence of selenium dioxide ($SeO_2$) in solvent and at temperatures ranging from 25° to 180° C., preferably 60° to 100° C. The selenium dioxide can be provided in any compatible solvent such as methylene chloride, methanol, ethylene dichloride, acetonitrile, chlorobenzene, ortho-dichlorobenzene, tetrachloroethylene or mixtures of these solvents. A full equivalent or excess of $SeO_2$ can be used to affect the conversion, or a catalytic amount of $SeO_2$ can be used in the presence of a co-oxidant such as tert-butylhydroperoxide, cumene hydroperoxide, hydrogen peroxide, N-methylmorpholine-N-oxide, air, or oxygen. Preferably, 1 to 50 mole % $SeO_2$ and more preferably 2 to 10 mole % $SeO_2$ based on the starting amount of the olefin derivative 2-methoxy-6-isopropenylnaphthalene is present in combination with 50 to 150 mole % of the co-oxidant present. One full equivalent of $SeO_2$ based on the starting amount of the olefin derivative is most preferred. Reaction times of 4 to 24 hours are preferred, with 12 to 16 hours most preferred.

The allylic alcohol derivative of Formula XI is isolated by cooling the reaction mixture to ambient temperature, filtering insoluble selenium compounds, and washing the organic layer first with an aqueous base and second, if a cooxidant hydroperoxide had been used, with an aqueous peroxide reducing agent. Suitable aqueous bases include aqueous sodium hydroxide, potassium hydroxide, potassium carbonate, sodium carbonate. Suitable reducing agents include aqueous $Na_2S_2O_3$, sodium sulfite, or sodium bisulfite. The organic layer is concentrated by vacuum distillation and the allylic alcohol derivative product of Formula XI is recovered by crystallization, distillation, or chromatography. Selenium compounds recovered from the reaction can be recycled for the next reaction after converting them back to selenium dioxide.

The allylic alcohol derivative of Formula XI can be converted directly to the aldehyde derivative 2-(6-methoxy-2-naphthyl)propionaldehyde of Formula IX depicted as Step P. Alternatively, the double bond of the allylic alcohol derivative can be removed by hydrogenation to form the alcohol derivative 2-(6-methoxy-2-naphthyl)propan-1-ol of Formula XII which can be oxidized in a second step to either the aldehyde derivative of Formula IX (Step R) or the propionic acid derivative of Formula X (Step S).

In Step P the allylic alcohol derivative of Formula XI is converted to the aldehyde derivative of Formula IX in the presence of a catalyst. Suitable catalysts to facilitate this conversion include $H_2Rh(PPh_3)_4$; $RuHCl(PPh_3)_3$; (1,5-cyclooctadiene)$Ir[PCH_3(C_6H_5)_2]_2^+PF_6^-$; $RuCl_3$ in the presence of sodium hydroxide; $[Rh(CO)_2Cl]_2$ in the presence of aqueous sodium hydroxide; and $[Ru_3O(OAc)_6(H_2O)_3]^+OAc^-$ to isomerize the double bond. Organic solvents such as benzene, toluene, dichloromethane, ethylene dichloride, acetone, tetrahydrofuran (THF), and dimethoxyethane (DME) can be used at temperatures of 25° to 100° C. depending on the catalyst. The preferred catalyst is (1,5-cyclooctadiene)$Ir[PCH_3(C_6H_5)_2]_2^+PF_6^-$ in THF or DME at 25° to 60° C. The catalyst is activated by exposure to hydrogen prior to the reaction. Reaction times are 0.5 to 24 hrs, and 4 to 8 hrs being preferred.

The aldehyde derivative product of Formula IX is isolated by concentration of the organic solution and crystallization, distillation, or chromatography of the residue.

Rather than converting the allylic alcohol derivative to the aldehyde derivative, in Step Q the allylic alcohol derivative of Formula XI is hydrogenated to the alcohol derivative 2-(6-methoxy-2-naphthyl)propan-1-ol of Formula XII. Catalysts for this reductive hydrogenation include palladium, platinum, and Raney nickel. The palladium and platinum metals may be supported on powdered carbon, alumina, calcium carbonate, formed supports, or other typical supports known in the art. The catalyst loading on the support may be 0.5 to 20 wt %, with 2 to 5 wt % being preferred. The supported catalyst can be used in 5 to 50 wt% based on the allylic alcohol derivative of Formula XI, with 5 to 10 wt % preferred. If Raney nickel is used, from 0.25 to 5 wt % catalyst based on the allylic alcohol derivative may be used, with 1 wt % preferred. The hydrogen may be supplied in the form of hydrogen gas, or it may be supplied by using "transfer hydrogenation" conditions in which the hydrogen is formed by the in-situ decomposition of formic acid, ammonium formate, diimide, or other hydrogen source. The preferred conditions utilize 5% palladium on alumina with hydrogen gas.

The organic solvents for the hydrogenation include methanol, ethanol, isopropanol, acetone, ethyl acetate, toluene, xylene, acetonitrile, acetic acid, tetrahydrofuran, and dimethoxyethane. Methanol or ethyl acetate are preferred. The temperature of the reduction can be 25° to 80° C., with 25° to 35° C. preferred. The pressure of the reduction can be from atmospheric to 700 kPa, with 130 to 275 kPa preferred.

The alcohol derivative of Formula XII can be isolated by filtering the catalyst from the reaction solution and concentrating the filtrate. The product may be purified by crystallization, distillation, or chromatography.

The alcohol derivative of Formula XII can be oxidized in Step R to form the aldehyde derivative of Formula I by any one of several methods known in the art for converting alcohols to aldehydes. These methods include using the following oxidation catalyst systems: oxalyl chloride $(COCl)_2$ in dimethylsulfoxide (DMSO) [known as the Swern oxidation]; air or oxygen in the presence of silver or gold catalysts; chromic acid; pyridinium chromate; pyridinium chlorochromate; pyridinium dichromate; pyridinium chlorochromate; ceric ammonium nitrate; silver carbonate; and aluminum triisopropoxide or tri-tert-butoxide and acetone [Oppenauer method]. The preferred method is to use oxalyl chloride in dimethylsulfoxide. The preferred solvent is dichloromethane and the preferred temperature is $-60°$ to $-20°$ C. Two to three equivalents each of $(COCl)_2$ and DMSO are used. The product is isolated by quenching the reaction at $-20°$ C. with triethylamine, warming the solution to ambient temperature, and washing the organic solution with water and dilute aqueous hydrochloric acid. Concentration of the organic layer gives the aldehyde derivative which can be purified by crystallization, distillation, or chromatography.

Alternatively, the alcohol derivative of Formula XII is oxidized in Step S to the propionic acid derivative of Formula X by any one of several methods known in the art for converting alcohols to carboxylic acids. These methods include oxidizing in the presence of chromic acid in acetic or sulfuric acid; pyridinium dichromate in dimethylformamide (DMF); potassium permanganate; ruthenium tetraoxide; hydrated ruthenium trichloride in the presence of sodium metaperiodate; silver oxide; and hydrogen peroxide. The preferred method is hydrated ruthenium trichloride in the presence of sodium metaperiodate in a mixed solvent system of acetonitrile, carbon tetrachloride, and water. The preferred reaction temperature is ambient with 1 to 5 mole % hydrated ruthenium trichloride and 3 to 6 equivalents sodium metaperiodate or potassium metaperiodate preferred. Reaction time is 1 to 8 hours, with 3 to 6 hours preferred. The propionic acid derivative product 2-(6-methoxy-2-naphthyl)propionic acid is isolated by extraction with dichloromethane or dichloroethane, concentration of the extract, and purification of the residue by crystallization, distillation, or chromatography.

The 2-(6-methoxy-2-naphthyl)propionic acid prepared via the above-described routes is a racemic mixture. The D- and L- enantiomers can be separated by any known resolution technique to form the D-2-(6-methoxy-2-naphthyl)propionic acid otherwise known as Naproxen. The intermediates prepared, including the new compound 2-(6-methoxy-2-naphthyl)prop-2-en-1-ol can be used for stereo-specific synthesis or other synthesis routes.

EXAMPLES

Example 1

Steps A and B: Synthesis of 2-hydroxy-6-(1-methylethyl)naphthalene from 2,6-diisopropylnaphthalene

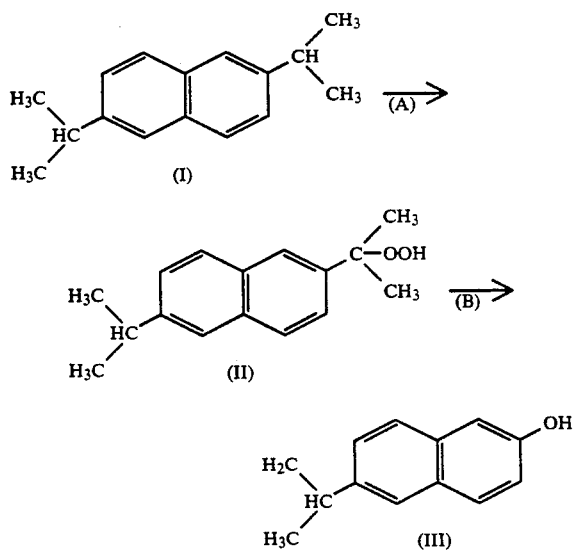

A mixture of 120 grams (g) 2,6-diisopropylnaphthalene, 120 milliliters (ml) heptane, 0.1 g 12% (by weight) Manganese CEM-ALL (Mooney Chemical), 1.5 g sodium carbonate ($Na_2CO_3$), and 0.5 ml 80% (by weight) cumene hydroperoxide was heated at 80° C. for 5 hours with an air sparge. At that time titration of a sample quenched in sodium iodide (NaI) saturated isopropanol with a 0.1 Normal (N) sodium thiosulfate solution indicated 30% peroxide content.

60 ml of methanol was added and a solution of 5 ml concentrated hydrochloric acid (HCl) in methyl alcohol was added dropwise while heating at reflux. When starch/potassium iodide paper showed no residual peroxides, the solution was cooled, toluene was added, and the methanol was removed under vacuum. The solution was extracted with 14% (by weight) alkaline soda, and the aqueous extract was acidified with concentrated HCl. The solid was collected by filtration and air dried, then recrystallized from a heptane/ethylacetate solution to give 2-hydroxy-6-(1-methylethyl)naphthalene, a white solid, mp 109° to 110° C.

$^{13}C$ Nuclear Magnetic Resonance (NMR) of 2-hydroxy-6-(1-methylethyl)naphthalene: 152.69 (s), 144.09 (s), 133.08 (s), 129.46 (d), 129.10 (s), 126.43 (d), 126.34 (d), 123.97 (d), 117.60 (d), 109.38 (d), 33.99 (d), 23.93 (q).

EXAMPLE 2

Step C: Conversion of 2-hydroxy-6-(1-methylethyl)nachthalene to 2-methoxy-6-isopropylnaphthalene.

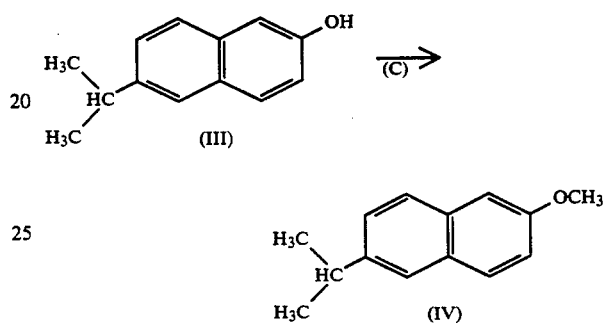

To a suspension of 31.71 g 2-hydroxy-6-(1-methylethyl)naphthalene in 500 ml water and under a nitrogen atmosphere was added 61.5 g of 14.4% (by weight) sodium hydroxide (NaOH). The mixture was heated to 60° C. and 30.02 g of dimethylsulfate was added in one portion to the dark cloudy solution. In 20 minutes the pH of the reaction had dropped from 13 to 2. Another 20 g 14.4% NaOH was added. After 45 minutes 10 g additional dimethylsulfate was added. After 1 hour 20 g of 14.4% NaOH was added and the reaction was heated at 80° C. overnight. The brown suspension was then extracted with toluene and the extract was dried over magnesium sulfate ($MgSO_4$), filtered, and concentrated in vacuum to give a crude solid which was recrystallized from isopropanol to give 2-methoxy-6-isopropylnaphthalene, melting point 63.5° to 64.5° C.

$^{13}C$ NMR of 2-methoxy-6-isopropylnaphthalene: 157.14 (s), 143.97 (s), 133.06 (s), 129.13 (s), 129.01 (d), 126.69 (d), 126.13 (d), 123.92 (d), 118.51 (d), 105.67 (d), 55.18 (q), 33.99 (d), 23.97 (q).

Shape Selective Catalysis of 2-methoxy-6-isopropylnaphthalene:

A 450 ml autoclave was charged with 158 g 2-methoxynapthalene and 3.2 g dealuminized mordenite catalyst. The autoclave was pressurized to 670 kPa with propylene then heated to 225° C. with agitation. Propylene was added as it was consumed to maintain pressure. In 8 hours, the conversion was 12% with 34% selectivity to 2-methoxy-6-isopropylnaphthalene (as confirmed by gas chromatography). Repetition of the reaction at 275° C. gave 19% conversion in 3 hours with 31% selectivity.

EXAMPLE 3

Step D: Hydroperoxidation of 2-methoxy-6-isopropylnaphthalene to form 2-methoxy-6-(1-hydroperoxy-1-methylethyl)naphthalene

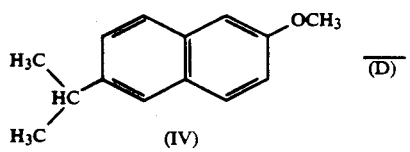

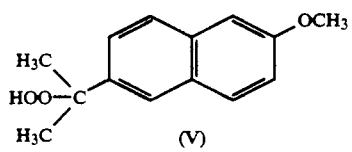

A solution of 120 g 2-methoxy-6-isopropylnaphthalene in 120 ml heptane is heated at 80° C. with an air sparge in the presence of Manganese CEM-ALL (Mooney Chemical), sodium carbonate, and a small amount of 80% (by weight) cumene hydroperoxide as an initiator until titration of an aliquot quenched in sodium iodide saturated isopropanol with 0.1 N sodium thiosulfate solution indicates 15 to 20% peroxide content in the reaction. The solution is cooled and filtered and the filtrate is used in the epoxidation reaction after concentration to remove some heptane.

By-products isolated from the hydroperoxidation include 2-acetyl-6-methoxynaphthalene and 6-(1-hydroxy-1-methylethyl)-2-methoxynaphthalene, whose structures were confirmed by comparison to physical properties of authentic materials [made by the acetylation of 2-methoxynaphthalene with acetyl chloride in nitrobenzene in the presence of aluminum chloride (*Organic Synthesis*, 53, 5)]. The tertiary alcohol was made by the action of methyl lithium on 2-acetyl-6-methoxynapthalene].

$^{13}$C NMR of 2-acetyl-6-methoxynaphthalene: 197.64 (s), 159.68 (s), 137.18 (s), 132.56 (s), 131.00 (d), 129.91 (d), 127.74 (s), 126.98 (d), 124.55 (d), 119.59 (d), 105.71 (d), 55.29 (q), 26.40 (q).

$^{13}$C NMR of 6-(1-hydroxy-1-methylethyl)-2-methoxynaphthalene: 157.51 (s), 144.21 (s), 133.30 (S), 129.52 (d), 128.55 (s), 126.71 (d), 123.97 (d), 122.23 (d), 118.72 (d), 105.51 (d), 72.44 (s), 55.21 (q), 31.60 (q).

EXAMPLE 4

Step H: Dehydrogenation of 2-methoxy-6-isopropylnaphthalene to yield 2-methoxy-6-isopropenylnaphthalene

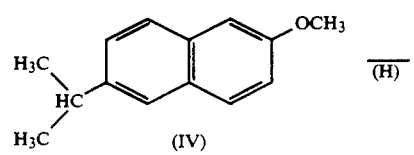

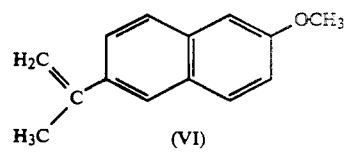

A hot tube reactor was packed with 43.1 g of iron oxide based dehydrogenation catalyst (United Catalysts, Inc. G-64C 3/16" extrudate ground to 20 to 32 mesh). A 5% (by weight) solution of 2-methoxy-6-isopropylnaphthalene in benzene was pumped (0.33 milliliters per minute (ml/min)) into the reactor along with water (0.78 ml/min) at 500° C. Gas chromatography analysis of the effluent indicated 40% conversion of the starting material with 50% selectivity to 2-methoxy-6-isopropenylnaphthalene.

EXAMPLE 5

Step I: Epoxidation of 2-methoxy-6-isopropenylnaphthalene to form 2-(6-methoxy-2-naphthyl)-1-propylene oxide

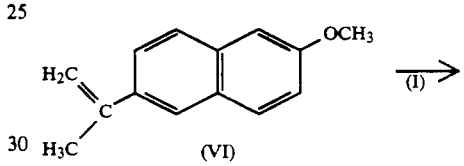

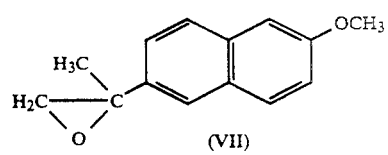

A solution of 1.00 g 2-methoxy-6-isopropenylnaphthalene in 32 ml ethylene dichloride (EDC) containing 15.9 mg molybdenum hexacarbonyl ((Mo(CO)$_6$)) and 82 mg triethylamine was heated to reflux. To the solution was added 3.12 ml of a solution of tert-butyl hydroperoxide in isooctane (3.0 M) in one portion. After 23 minutes the reaction was quenched by pouring the mixture into 300 ml of 5% sodium sulfite (Na$_2$SO$_3$) at 10° C. The flask was rinsed with two 15 ml portions of EDC and 50 ml additional EDC was added to the mixture. The layers were separated and the aqueous layer was back extracted with 100 ml EDC. The combined organic extracts were washed with 100 ml water then dried over magnesium sulfate (MgSO$_4$), filtered, and concentrated to give a residue which was purified on a 4.5 × 12 cm Silica (SiO$_2$) chromatography column using a 5 to 1 by volume heptane:ethyl acetate solution as the eluent. The product containing fractions were concentrated to give the epoxide derivative VII. The $^1$H and $^{13}$C NMR of the product confirmed the structure. Further proof was obtained by comparison of the NMR of the product to the NMR of the epoxide made by the action of trimethylsulfoxonium iodide and potassium tert-butoxide on 2-acetyl-6-methoxynaphthalene.

The reaction conditions for Steps E and J are similar to the epoxidation of Step I differing only as to the choice of the starting peroxide and olefin derivatives.

$^1$H NMR of 2-methoxy-6-isopropenylnaphthalene: 1.78 (s, 3H), 2.86 (d, 1H), 3.00 (d, 1H), 3.87 (s, 3H), 7.08–7.75 (m, 6H).

13C NMR of 2-(6-methoxy-2-naphthyl)-1-propylene oxide: 157.72 (s), 136.25 (s), 133.83 (s), 129.32 (d), 128.55 (s), 126.89 (d), 124.23 (d), 123.63 (d), 118.97 (d), 105.57 (d), 56.95 (t*), 56.81 (s*), 55.19 (q), 21.83 (q) (*indicates assignments may be reversed).

EXAMPLE 6

Step K: Dehydration of the tertiary alcohol derivative 2-methoxy-6-(1-hydroxy-1-methylethyl)naphthalene to form the olefin derivative 2-methoxy-6-isopropenylnaphthalene

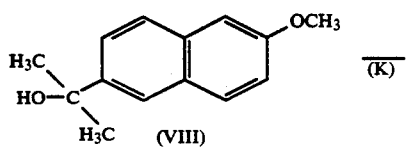

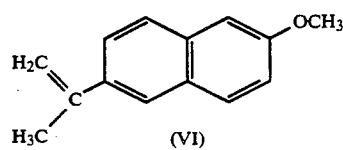

A solution of 1.22 g 2-methoxy-6-(1-hydroxy-1-methylethyl)naphthalene in 25 ml hexamethylphosphoramide (HMPA) was heated to 240° C. for 15 minutes. The solution was cooled, poured into water, and the brown solid which had formed was filtered off and washed with isopropanol. Recrystallization of the brown solid from isopropanol gave 2-methoxy-6-isopropenylnaphthalene, mp 101° to 103 5° C.

A solution of 5.00 g 2-methoxy-6-(1-hydroxy-1-methylethyl)naphthalene in 60 ml dimethylformamide with 0.5 ml pyridine and 3.70 g pyridine hydrobromide was heated at 80° C. for 3.5 hr. The solution was cooled and poured into 200 ml ice water. The resulting mixture was extracted twice with 150 ml ether and the combined ether extracts were washed twice with 100 ml water. The organic layer was dried over MgSO4 and filtered. 30 ml of a 10 to 1 by volume heptane/ethyl acetate mixture was added to the filtrate. The solution was concentrated to remove ether and then cooled to precipitate the product, 2-methoxy-6-isopropenylnaphthalene.

13C NMR of 2-methoxy-6-isopropenylnaphthalene: 157.72 (s), 142.96 (s), 136.22 (s), 133.94 (s), 129.70 (d), 128.79 (s), 126.54 (d), 124.35 (d), 124.07 (d), 118.80 (d), 112.06 (t), 105.68 (d), 55.24 (q), 21.84 (q).

EXAMPLE 7

Step F: Conversion of 2-(6-methoxy-2-naphthyl)-1-propylene oxide to 2-(6-methoxy-2-naphthyl)propionaldehyde

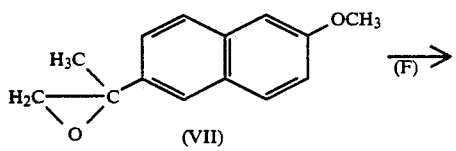

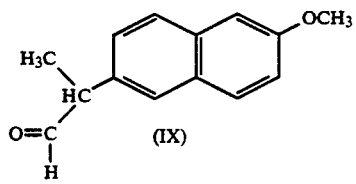

The 2-(6-methoxy-2-naphthyl)-1-propylene oxide is dissolved in tetrahydrofuran purged with nitrogen and cooled to a temperature ranging from 0° to 30° C., and preferably 5° to 0° C. A solution of boron trifluoride etherate in tetrahydrofuran is added to the mixture while stirring. After stirring for about 30 minutes, pyridine is added to the mixture and the mixture is concentrated by distillation under reduced pressure wherein the concentrate contains the 2-(6-methoxy-2-naphthyl)-propionaldehyde of Formula IX.

EXAMPLE 8

Step G: Conversion of the aldehyde derivative 2-(6-methoxy-2-naphthyl)propionaldehyde to the acid derivative 2-(6-methoxy-2-naphthyl)propionic acid

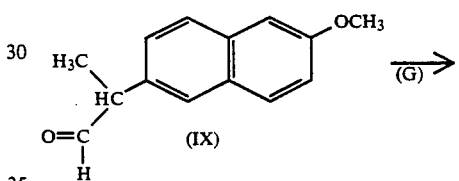

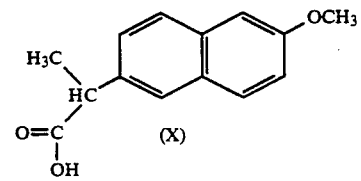

A solution of 0.20 g 2-(6-methoxy-2-naphthyl)propionaldehyde with 0.20 g hydroxylamine hydrochloride and 0.20 g pyridine in 15 ml diethylene glycol is heated at 100° C. for hr. The reaction is then heated to 160° C. after adding 0.25 g of 85% by weight potassium hydroxide. Ammonia is evolved and heating is continued for 2 hr. The solution is cooled and poured into 100 ml ice cold dilute HCl. The 2-(6-methoxy-2-naphthyl)propionic acid which forms is collected by filtration, washed with water, and air dried.

EXAMPLE 9

Step O: Conversion of 2-methoxy-6-isopropenylnaphthalene to 2-(6-methoxy-2-naphthyl)prop-2-en-1-ol

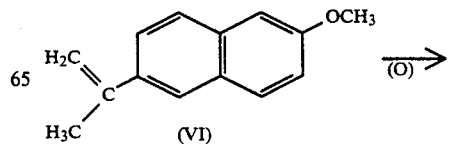

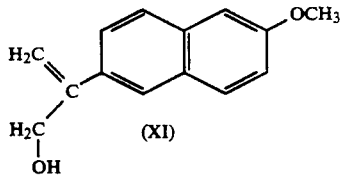

A solution of 0.20 g 2-methoxy-6-isopropenylnaphthalene and 0.12 g selenium dioxide (SeO₂) in 10 ml methylene chloride was heated at reflux for 22 hours. The cooled solution was then washed with 10 ml 20% (by weight) sodium hydroxide (NaOH) after adding 40 ml ethylene dichloride (EDC). The organic layer was dried over MgSO₄, filtered, and concentrated to give an oil which was purified on a 2×17 cm silica (SiO₂) column using a 5 to 1 by volume solution of heptane and ethyl acetate. The product containing fractions were combined and concentrated to give 2-(6-methoxy-2-naphthyl)prop-2-en-1-ol.

¹H NMR of 2-(6-methoxy-2-naphthyl)prop-2-en-1-ol: 3.92 (s, 3H), 4.65 (s, 2H), 5.40 (s, 1H), 7–8 (m, 7H).

¹³C NMR: 157.74 (s), 147.03 (s), 134.34 (s), 133.60 (s), 129.74 (d), 128.87 (s), 126.98 (d), 124.82 (d), 124.66 (d), 119.07 (d), 112.43 (t), 105.72 (d), 65.25 (t), 55.29 (q).

EXAMPLE 10

Step P: Conversion of
2-(6-methoxy-2-naphthyl)prop-2-en-1-ol to
2-(6-methoxy-2-naphthyl)propionaldehyde

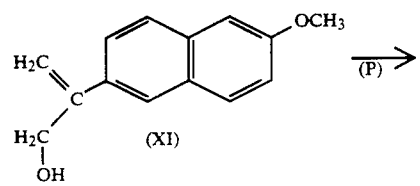

A solution of 0.21 g 2-(6-methoxy-2-naphthyl)prop-2-en-1-ol is stirred with 10 mg of (1,5-cyclooctadiene)Ir[PCH₃(C₆H₅)₂]₂+PF₆⁻ (preactivated with hydrogen) in 10 ml tetrahydrofuran at 60° C. for 6 hr. The solution is then concentrated to give the aldehyde derivative 2-(6-methoxy-2-naphthyl)propionaldehyde.

EXAMPLE 11

Step Q: Conversion of
2-(6-methoxy-2-naphthyl)prop-2-en-1-ol to
2-(6-methoxy-2-naphthyl)propan-1-ol.

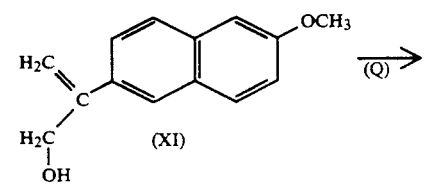

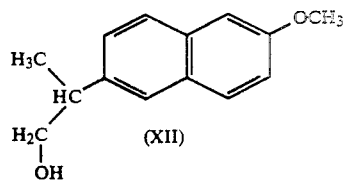

A solution of 50 mg of 2-(6-methoxy-2-naphthyl)-prop-2-en 1-ol in 25 ml ethyl acetate was charged to a Parr bottle with 80 mg of 5% by weight palladium on alumina. The mixture enated on the Parr shaker at ambient temperature and 275 kPa for 2.25 hours then the catalyst was filtered off and the filtrate was concentrated to give 2-(6-methoxy-2-naphthyl)propan-1-ol.

¹³C NMR of 2-(6-methoxy-2-naphthyl)propan-1-ol: 157.33 (s), 138.77 (s), 133.44 (s), 129.01 (s and d), 127.04 (d), 126.22 (d), 125,73 (d), 118.74 (d), 105.60 (d), 68.42 (t), 55.20 (q), 42.26 (d), 17.57 (d).

EXAMPLE 12

Step R: Conversion of
2-(6-methoxy-2-naphthyl)propan-1-ol to
2-(6-methoxy-2-naphthyl)propionaldehyde

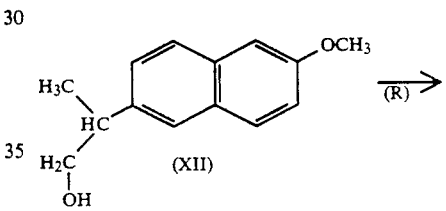

A solution g oxalyl chloride in 15 ml methylene chloride was cooled to −60° C. Using a syringe, 0.45 g of dimethylsulfoxide was added to the cold solution dropwise. After 5 minutes, a solution of 0.31 g of 2-(6-methoxy-2-naphthyl)propan-1-ol in 15 ml methylene chloride was added dropwise over 15 min. Ten minutes after the addition was completed the solution was carefully warmed to −20° C. and held for 10 min. The reaction was then quenched by adding 2 ml triethylamine. After warming to ambient temperature the solution was poured into 100 ml water. The organic layer was washed with 120 ml dilute HCl and 120 ml dilute potassium carbonate (K₂CO₃). The organic layer was dried over MgSO₄, filtered, and concentrated to give the aldehyde derivative 2-(6-methoxy-2-naphthyl)propionaldehyde.

¹³C NMR of 2-(6-methoxy-2-naphthyl)propionaldehyde: 200.64 (d), 157.57 (s), 133.59 (s), 132.47 (s), 128.90 (d and s), 127.37 (d), 126.66 (d), 126.36 (d), 118.94 (d), 105.40 (d), 54.92 (q), 52.51 (d), 14.29 (q).

EXAMPLE 13

Step S: Conversion of
2-(6-methoxy-2-naphthyl)propan-1-ol to
2-(6-methoxy-2-naphthyl)propionic acid

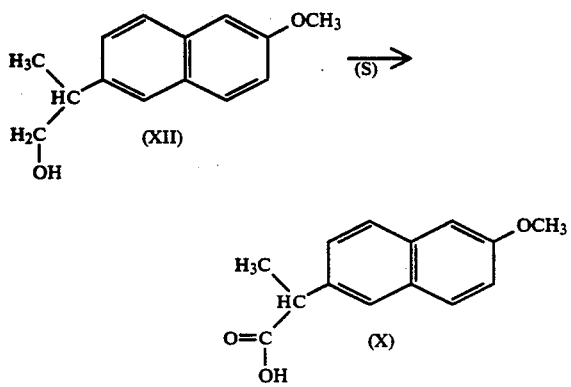

To a solution of 0.21 g 2-(6-methoxy-2-naphthyl)propan-1-ol in 2 ml of carbon tetrachloride, 2 ml acetonitrile, 3 ml of water, and 0.877 g of sodium metaperiodate is added 5 mg of ruthenium trichloride hydrate. After 4 hours at ambient temperature the mixture is extracted with 4 portions of 10 ml of methylene chloride. The combined organic extracts are dried over MgSO$_4$, filtered, and concentrated to give the product 2-(6-methoxy-2-naphthyl)propionic acid.

From the foregoing it will be seen that this invention is one well adapted to attain all ends and objects hereinabove set forth together with the other advantages which are obvious and which are inherent to the various routes delt will be understood that certain reaction steps described.

It will be understood that certain reaction steps and subcombinations of steps are of utility and may be employed without reference to other reaction steps an subcombinations of steps. This is contemplated by and is within the scope of the claims.

Since many possible embodiments ma be made of the invention without departing from the scope thereof, it is to be understood that all matter herein set forth is to be interpreted as illustrative and not in a limiting sense.

Having thus described the invention, I claim:

1. A process for making 2-(6-methoxy-2-naphthyl)propionic acid, said process comprising the steps of:
   (A) hydroperoxidizing 2,6-diisopropylnaphthalene in the presence of oxygen and a catalyst to form the product 2-(1-hydroperoxy-1-methylethyl)-6-(1-methylethyl)naphthalene;
   (B) converting said product of step (A) by heating said 2-(1-hydroperoxy-1-methylethyl)-6-(1-methylethyl)naphthalene in the presence of an acid catalyst to the product 2-hydroxy-6-(1-methylethyl)naphthalene;
   (C) alkylating said product to step (B) in the presence of a base and a methyl donor to form the product 2-methoxy-6-isopropylnaphthalene;
   (D) converting said product of step (C) to the product 2-(6-methoxy-2-naphthyl)-1-propylene oxide by hydroperoxidizing the product of step (C) is the presence of oxygen and a catalyst to form the peroxide derivative 2-methoxy-6-(1-hydroperoxy-1-methyethyl)naphthalene; and
converting said peroxide derivative 2-methoxy-6-(1-hydroperoxy-1-methylethyl)naphthalene to the epoxide derivative product 2-(6-methoxy-2-naphthyl)-1-propylene oxide by reacting said peroxide derivative with 2-methoxy-6-isopropenylnaphthalene to form 2-(6-methoxy-2-naphthyl)-1-propylene oxide plus the tertiary alcohol derivative 2-methoxy-6-(1-hydroxy-1-methylethyl)naphthalene;
   (E) converting said product to step (D) to the product 2-(6-methoxy-2-naphthyl)propionaldehyde by heating said 2-(6-methoxy-2-naphthyl)-1-propylene oxide; and
   (F) oxidizing said 2-(6-methoxy-2-naphthyl)propionaldehyde in the presence of a chromic acid solution to form 2-(6-methoxy-2-naphthyl)propionic acid.

2. A process according to claim 1 wherein said catalyst comprises the alkali earth metal salt of an organic or inorganic acid.

3. A process according to claim 2 wherein said acid comprises one or more of the following: carboxylic acid, sulfonic acid and phosphoric acid.

4. A process according to claim 1 wherein said hydroperoxidizing step additionally occurs in the presence of a reaction initiator.

5. A process according to claim 4 wherein said reaction initiator is an organic free radical former selected from the group consisting of peroxides and azo compounds.

6. A process according to claim 1 wherein said hydroperoxidizing step occurs at a temperature ranging from 20° to 160° C.

7. A process according to claim 6 wherein said hydroperoxidizing step occurs at a temperature ranging from 80° to 120° C.

8. A process according to claim 1 wherein said oxygen is added to the reaction system by sparging the system with an oxygen containing gas under pressure.

9. A process according to claim 1 wherein said hydroperoxidizing step additionally occurs in the presence of a solvent.

10. A process according to claim 1 wherein said hydroperoxidizing step additionally occurs in the presence of a base.

11. A process according to claim 1 wherein said hydroperoxidizing step is halted by cooling the reaction mixture after reaching a percent of conversion of 10 to 35% 2-(1-hydroperoxy-1-methylethyl)-6-(1-methylethyl)naphthalene from 2,6-diisopropylnaphthalene.

12. A process according to claim 1 wherein said acid catalyst comprises a mineral acid.

13. A process according to claim 12 wherein said acid catalyst comprises one or more of the following: hydrochloric acid, sulfuric acid, phosphoric acid and perchloric acid.

14. A process according to claim 1 wherein the reaction mixture is heated to a temperature ranging from 20° to 140° C.

15. A process according to claim 14 wherein said reaction mixture is heated to about reflux temperatures.

16. A process according to claim 1 wherein said methyl donor is capable of alkylating an anion.

17. A process according to claim 19 wherein said methyl donor comprises one or more of the following: dimethyl sulfate, methyl iodide, methyl chloride, methyl bromide, methyl sulfonate, methyl tosylate, methyl triflate and methyl bisulfate.

18. A process according to claim 1 wherein said alkylation occurs at about reflux temperature.

19. A process according to claim 16 wherein said alkylation occurs at a temperature ranging from 20° to 120° C.

20. A process according to claim 1 wherein said alkylation step additionally occurs in the presence of a compatible solvent.

21. A process according to claim 20 wherein said solvent comprises one or more of the following: water, tetrahydrofuran, hexamethylphosphoric triamide, dimethylsulfoxide, N,N-dimethylformamide and dioxane.

22. A process according to claim 1 wherein said 2-methoxy-6-isopropylnaphthalene is precipitated by cooling the reaction mixture.

23. A process according to claim 1 wherein said hydroperoxidizing step is halted by cooling the reaction mixture after reaching a percent of conversion from 2-methoxy-6-isopropylnaphthalene to 2-methoxy-6-(1-hydroperoxy-1-methylethyl)naphthalene of 10 to 35%.

24. A process according to claim 1 wherein said reacting step comprises reacting said 2-methoxy-6-(1-hydroperoxy-1-methylethyl)naphthalene and 2-methoxy-6-isopropenylnaphthalene in the presence of a solvent and an oxidation catalyst.

25. A process according to claim 24 wherein said solvent comprises one or more of the following: ethylene dichloride, toluene and xylene.

26. A process according to claim 24 wherein said oxidation catalyst comprises one or more of the following: molybdenum and vanadium catalysts.

27. A process according to claim 26 wherein said catalyst comprises one or more of the following: molybdenum hexacarbonyl, molybdenum acetylacetonate, molybdenum trioxide, molybdenum blue, and vanadyl acetylacetonate.

28. A process according to claim 24 wherein said reacting step additionally occurs in the presence of an acid scavenger.

29. A process according to claim 28 wherein said acid scavenger comprises one or more of the following: disodium hydrogen phosphate and a tertiary amine.

30. A process according to claim 29 wherein said reacting step occurs at a temperature ranging form 20° to 120° C.

31. A process according to claim 1 wherein said 2-(6-methoxy-2-naphthyl)-1-propylene oxide is heated to a temperature above about 220° C.

32. A process according to claim 1 wherein said 2-(6-methoxy-2-naphthyl)-1-propylene oxide is heated to a temperature above about 120° C. in the presence of a Lewis acid.

33. A process according to claim 1 wherein said 2-(6-methoxy-2-naphthyl)-1-propylene oxide is heated in the presence of an inert organic solvent.

34. A process according to claim 1 wherein said chromic acid solution has a normality ranging from 6 to 10.

35. A process according to claim 1 wherein said oxidizing step takes place at temperatures ranging from $-20°$ to $10.0°$ C.

36. A process for making 2-(6-methoxy-2-naphthyl)-propionic acid, said process comprising the steps of:
(A) hydroperoxidizing 2,6-diisopropylnaphthalene in the presence of oxygen and a catalyst to form the product 2-(1-hydroperoxy-1-methylethyl)-6-(1-methylethyl)naphthalene;
(B) converting said product of step (A) by heating said 2-(1-hydroperoxy-1-methylethyl)-6-(1-methylethyl)naphthalene in the presence of an acid catalyst to the product 2-hydroxy-6-(1-methylethyl)naphthalene;
(C) alkylating said product of step (B) in the presence of a base and a methyl donor to form the product 2-methoxy-6-isopropylnaphthalene;
(D) converting said product of step (C) to the product 2-(6-methoxy-2-naphthyl)-1-propylene oxide by hydroperoxidizing the product of step (C) in the presence of oxygen and a catalyst to form the peroxide derivative 2-methoxy-6-(1-hydroperoxy-1-methylethyl)naphthalene; and
converting said peroxide derivative 2-methoxy-6-(1-hydroperoxy-1-methylethyl)naphthalene to the epoxide derivative product 2-(6-methoxy-2-naphthyl)-1-propylene oxide by reacting said peroxide derivative with 2-methoxy-6-isopropenylnaphthalene to form 2-(6-methoxy-2-naphthyl)-1-propylene oxide plus the tertiary alcohol derivative 2-methoxy-6-(1-hydroxy-1-methylethyl)naphthalene;
(E) converting said product of step (D) to the product 2-(6-methoxy-2-naphthyl)-1-propylene oxide in an inert organic solvent and mixing with a Lewis acid at temperatures ranging from 0° to 30° C.; and
(F) oxidizing said 2-(6-methoxy-2-naphthyl)propionaldehyde in the presence of a chromic acid solution to form 2-(6-methoxy-2-naphthyl)propionic acid.

* * * * *